(12) United States Patent
Heske et al.

(10) Patent No.: US 8,162,851 B2
(45) Date of Patent: Apr. 24, 2012

(54) BIOPSY NEEDLE SYSTEM HAVING A PRESSURE GENERATING UNIT

(75) Inventors: Norbert Heske, Kottgeisering (DE); Thomas Heske, Grafrath (DE)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/898,294

(22) Filed: Oct. 5, 2010

(65) Prior Publication Data

US 2011/0021946 A1 Jan. 27, 2011

Related U.S. Application Data

(63) Continuation of application No. 11/680,900, filed on Mar. 1, 2007, now Pat. No. 7,828,747, which is a continuation of application No. 10/549,818, filed as application No. PCT/EP2004/003328 on Mar. 29, 2004, now Pat. No. 7,762,961.

(30) Foreign Application Priority Data

Mar. 29, 2003 (DE) .................. 103 14 240

(51) Int. Cl.
*A61B 10/00* (2006.01)

(52) U.S. Cl. ......... 600/566; 600/562; 600/564; 600/565

(58) Field of Classification Search .................. 600/562, 600/564–568
See application file for complete search history.

(56) References Cited

U.S. PATENT DOCUMENTS

| 737,293 A | 8/1903 | Summerfeldt |
|---|---|---|
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |
| 4,275,730 A | 6/1981 | Hussein |
| 4,282,884 A | 8/1981 | Boebel |
| 4,354,092 A | 10/1982 | Manabe et al. |
| 4,445,509 A | 5/1984 | Auth |
| 4,490,137 A | 12/1984 | Moukheibir |
| 4,549,554 A | 10/1985 | Markham |

(Continued)

FOREIGN PATENT DOCUMENTS

DE 3924291 A1 1/1991

(Continued)

*Primary Examiner* — Jeffrey G Hoekstra

(57) ABSTRACT

A biopsy needle system includes a cylinder with an open end and a cylinder wall. A piston is inserted in the open end such that a cylinder interior volume is defined between the piston and the cylinder, the piston being movable in the cylinder. A biopsy needle is connected to the cylinder. A ventilation groove is established in the cylinder wall only to a depth of a portion of a thickness of the cylinder wall. The ventilation groove is positioned such that the cylinder interior volume of the cylinder communicates with the ambient atmosphere when the piston is displaced to a position in the cylinder so as to establish an airflow through the ventilation groove past the piston.

19 Claims, 2 Drawing Sheets

U.S. PATENT DOCUMENTS

| | | | |
|---|---|---|---|
| 4,577,629 A | 3/1986 | Martinez | |
| 4,589,414 A | 5/1986 | Yoshida et al. | |
| 4,603,694 A | 8/1986 | Wheeler | |
| 4,605,011 A | 8/1986 | Naslund | |
| 4,617,430 A | 10/1986 | Bryant | |
| 4,643,197 A | 2/1987 | Greene et al. | |
| 4,645,153 A | 2/1987 | Granzow et al. | |
| 4,678,459 A | 7/1987 | Onik et al. | |
| 4,696,298 A | 9/1987 | Higgins et al. | |
| 4,702,260 A | 10/1987 | Wang | |
| 4,844,087 A | 7/1989 | Garg | |
| 4,850,354 A | 7/1989 | McGurk-Burleson et al. | |
| 4,893,635 A | 1/1990 | de Groot et al. | |
| 4,907,598 A | 3/1990 | Bauer | |
| 4,940,061 A | 7/1990 | Terwilliger et al. | |
| 4,958,625 A | 9/1990 | Bates et al. | |
| 4,967,762 A | 11/1990 | DeVries | |
| 4,986,278 A | 1/1991 | Ravid et al. | |
| 4,986,279 A | 1/1991 | O'Neill | |
| 4,986,807 A | 1/1991 | Farr | |
| 4,989,614 A | 2/1991 | Dejter, Jr. et al. | |
| 5,025,797 A | 6/1991 | Baran | |
| 5,125,413 A | 6/1992 | Baran | |
| 5,138,245 A | 8/1992 | Mattinger et al. | |
| 5,158,528 A | 10/1992 | Walker et al. | |
| 5,176,628 A | 1/1993 | Charles et al. | |
| 5,225,763 A | 7/1993 | Krohn et al. | |
| 5,234,000 A | 8/1993 | Hakky et al. | |
| 5,236,334 A | 8/1993 | Bennett | |
| 5,282,476 A | 2/1994 | Terwilliger | |
| 5,282,477 A | 2/1994 | Bauer | |
| 5,324,306 A | 6/1994 | Makower et al. | |
| 5,334,183 A | 8/1994 | Wuchinich | |
| 5,368,029 A | 11/1994 | Holcombe et al. | |
| 5,368,045 A | 11/1994 | Clement et al. | |
| 5,400,798 A | 3/1995 | Baran | |
| 5,439,474 A | 8/1995 | Li | |
| 5,458,112 A | 10/1995 | Weaver | |
| 5,469,860 A | 11/1995 | De Santis | |
| 5,479,486 A | 12/1995 | Saji | |
| 5,485,917 A | 1/1996 | Early | |
| 5,492,130 A | 2/1996 | Chiou | |
| 5,496,860 A | 3/1996 | Matsumoto et al. | |
| 5,511,556 A | 4/1996 | DeSantis | |
| 5,526,822 A | 6/1996 | Burbank et al. | |
| 5,535,755 A | 7/1996 | Heske | |
| 5,546,957 A | 8/1996 | Heske | |
| 5,554,151 A | 9/1996 | Hinchliffe | |
| 5,560,373 A | 10/1996 | De Santis | |
| 5,564,436 A | 10/1996 | Hakky et al. | |
| 5,575,293 A | 11/1996 | Miller et al. | |
| 5,601,585 A | 2/1997 | Banik et al. | |
| 5,602,449 A | 2/1997 | Krause et al. | |
| 5,617,874 A | 4/1997 | Baran | |
| 5,649,547 A | 7/1997 | Ritchart et al. | |
| 5,655,542 A | 8/1997 | Weilandt | |
| 5,655,657 A | 8/1997 | Roshdy | |
| 5,665,101 A | 9/1997 | Becker et al. | |
| 5,699,909 A | 12/1997 | Foster | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A | 5/1998 | Murphy-Chutorian | |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,788,651 A | 8/1998 | Weilandt | |
| 5,792,167 A | 8/1998 | Kablik et al. | |
| 5,807,282 A | 9/1998 | Fowler | |
| 5,817,033 A | 10/1998 | DeSantis et al. | |
| 5,817,034 A | 10/1998 | Milliman et al. | |
| 5,823,970 A | 10/1998 | Terwilliger | |
| 5,827,305 A | 10/1998 | Gordon | |
| 5,830,219 A | 11/1998 | Bird et al. | |
| D403,405 S | 12/1998 | Terwilliger | |
| 5,857,982 A | 1/1999 | Milliman et al. | |
| 5,908,233 A | 6/1999 | Heskett et al. | |
| 5,913,857 A | 6/1999 | Ritchart et al. | |
| 5,916,229 A | 6/1999 | Evans | |
| 5,928,164 A | 7/1999 | Burbank et al. | |
| 5,944,673 A | 8/1999 | Gregoire et al. | |
| 5,951,490 A | 9/1999 | Fowler | |
| 5,951,575 A | 9/1999 | Bolduc et al. | |
| 5,964,716 A | 10/1999 | Gregoire et al. | |
| 5,971,939 A | 10/1999 | DeSantis et al. | |
| 5,976,164 A | 11/1999 | Bencini et al. | |
| 5,980,469 A | 11/1999 | Burbank et al. | |
| 6,007,495 A | 12/1999 | Matula | |
| 6,007,497 A | 12/1999 | Huitema | |
| 6,007,556 A | 12/1999 | Kablik et al. | |
| 6,017,316 A | 1/2000 | Ritchart et al. | |
| 6,018,227 A | 1/2000 | Kumar et al. | |
| 6,019,733 A | 2/2000 | Farascioni | |
| 6,022,324 A | 2/2000 | Skinner | |
| 6,022,325 A | 2/2000 | Siczek et al. | |
| 6,027,458 A | 2/2000 | Janssens | |
| 6,036,657 A | 3/2000 | Milliman et al. | |
| 6,050,955 A | 4/2000 | Bryan et al. | |
| 6,077,230 A | 6/2000 | Gregoire et al. | |
| 6,083,176 A | 7/2000 | Terwilliger | |
| 6,083,237 A | 7/2000 | Huitema et al. | |
| 6,086,544 A | 7/2000 | Hibner et al. | |
| 6,106,484 A | 8/2000 | Terwilliger | |
| 6,110,129 A | 8/2000 | Terwilliger | |
| 6,120,462 A | 9/2000 | Hibner et al. | |
| 6,123,957 A | 9/2000 | Jernberg | |
| 6,126,617 A | 10/2000 | Weilandt et al. | |
| 6,142,955 A | 11/2000 | Farascioni et al. | |
| 6,162,187 A | 12/2000 | Buzzard et al. | |
| 6,165,136 A | 12/2000 | Nishtala | |
| 6,193,673 B1 | 2/2001 | Viola et al. | |
| 6,196,978 B1 | 3/2001 | Weilandt et al. | |
| 6,213,957 B1 | 4/2001 | Milliman et al. | |
| 6,220,248 B1 | 4/2001 | Voegele et al. | |
| 6,231,522 B1 | 5/2001 | Voegele et al. | |
| 6,241,687 B1 | 6/2001 | Voegele et al. | |
| 6,273,861 B1 | 8/2001 | Bates et al. | |
| 6,273,862 B1 | 8/2001 | Privitera et al. | |
| 6,280,398 B1 | 8/2001 | Ritchart et al. | |
| 6,283,925 B1 | 9/2001 | Terwilliger | |
| 6,322,523 B2 | 11/2001 | Weilandt et al. | |
| 6,328,701 B1 | 12/2001 | Terwilliger | |
| 6,331,166 B1 | 12/2001 | Burbank et al. | |
| 6,358,217 B1 | 3/2002 | Bourassa | |
| 6,402,701 B1 | 6/2002 | Kaplan et al. | |
| 6,419,641 B1 | 7/2002 | Mark et al. | |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdorff et al. | |
| 6,436,054 B1 | 8/2002 | Viola et al. | |
| 6,482,158 B2 | 11/2002 | Mault | |
| 6,485,436 B1 | 11/2002 | Truckai et al. | |
| 6,488,636 B2 | 12/2002 | Bryan et al. | |
| 6,527,736 B1 | 3/2003 | Attinger et al. | |
| 6,540,694 B1 | 4/2003 | Van Bladel et al. | |
| 6,540,761 B2 | 4/2003 | Houser | |
| 6,551,255 B2 | 4/2003 | Van Bladel et al. | |
| 6,554,779 B2 | 4/2003 | Viola et al. | |
| 6,585,664 B2 | 7/2003 | Burdorff et al. | |
| 6,638,235 B2 | 10/2003 | Miller et al. | |
| 6,659,105 B2 | 12/2003 | Burbank et al. | |
| 6,659,338 B1 | 12/2003 | Dittmann et al. | |
| 6,683,439 B2 | 1/2004 | Takano et al. | |
| 6,689,072 B2 | 2/2004 | Kaplan et al. | |
| 6,695,786 B2 | 2/2004 | Wang et al. | |
| 6,712,773 B1 | 3/2004 | Viola | |
| 6,752,768 B2 | 6/2004 | Burdorff et al. | |
| 6,753,671 B1 | 6/2004 | Harvey | |
| 6,758,824 B1 | 7/2004 | Miller et al. | |
| 6,764,495 B2 | 7/2004 | Lee et al. | |
| 6,832,990 B2 | 12/2004 | Kortenbach et al. | |
| 6,849,080 B2 | 2/2005 | Lee et al. | |
| 6,908,440 B2 | 6/2005 | Fisher | |
| D508,458 S | 8/2005 | Solland et al. | |

| | | |
|---|---|---|
| 6,926,676 B2 | 8/2005 | Turturro et al. |
| 6,984,213 B2 | 1/2006 | Horner et al. |
| 7,025,732 B2 | 4/2006 | Thompson et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,276,032 B2 | 10/2007 | Hibner |
| 7,328,794 B2 | 2/2008 | Lubs et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,828,746 B2 | 11/2010 | Teague |
| 7,854,706 B2 | 12/2010 | Hibner |
| 7,883,476 B2 | 2/2011 | Miller et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0045840 A1 | 4/2002 | Voegele et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0120212 A1 | 8/2002 | Ritchart et al. |
| 2002/0151822 A1 | 10/2002 | Burdorff et al. |
| 2002/0156395 A1 | 10/2002 | Stephens et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0186393 A1 | 9/2004 | Leigh et al. |
| 2004/0215103 A1 | 10/2004 | Mueller, Jr. et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Scwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118049 A1 | 5/2007 | Viola |
| 2007/0149893 A1 | 6/2007 | Heske et al. |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0306406 A1 | 12/2008 | Thompson et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0125062 A1 | 5/2009 | Arnin |
| 2009/0137927 A1 | 5/2009 | Miller |

| | | | |
|---|---|---|---|
| 2009/0163829 A1 | 6/2009 | Seiger et al. | |
| 2009/0227893 A1 | 9/2009 | Coonahan et al. | |
| 2010/0063416 A1 | 3/2010 | Cicenas et al. | |
| 2010/0106055 A1 | 4/2010 | Heske et al. | |
| 2010/0152611 A1 | 6/2010 | Parihar et al. | |
| 2010/0160820 A1 | 6/2010 | Weikel, Jr. et al. | |
| 2010/0292607 A1 | 11/2010 | Moore et al. | |
| 2010/0312140 A1 | 12/2010 | Smith et al. | |
| 2011/0152715 A1 | 6/2011 | Delap et al. | |
| 2011/0160611 A1 | 6/2011 | Ritchart et al. | |

FOREIGN PATENT DOCUMENTS

| | | |
|---|---|---|
| DE | 4041614 C1 | 10/1992 |
| DE | 10034297 A1 | 4/2001 |
| DE | 10026303 A1 | 2/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1665989 A2 | 6/2006 |
| EP | 2095772 A1 | 2/2009 |
| EP | 2106750 A2 | 10/2009 |
| FR | 1345429 A | 12/1963 |
| FR | 2739293 A1 | 4/1997 |
| GB | 2018601 A | 10/1979 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9628097 A1 | 9/1996 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |
| WO | 2008131362 A2 | 10/2008 |

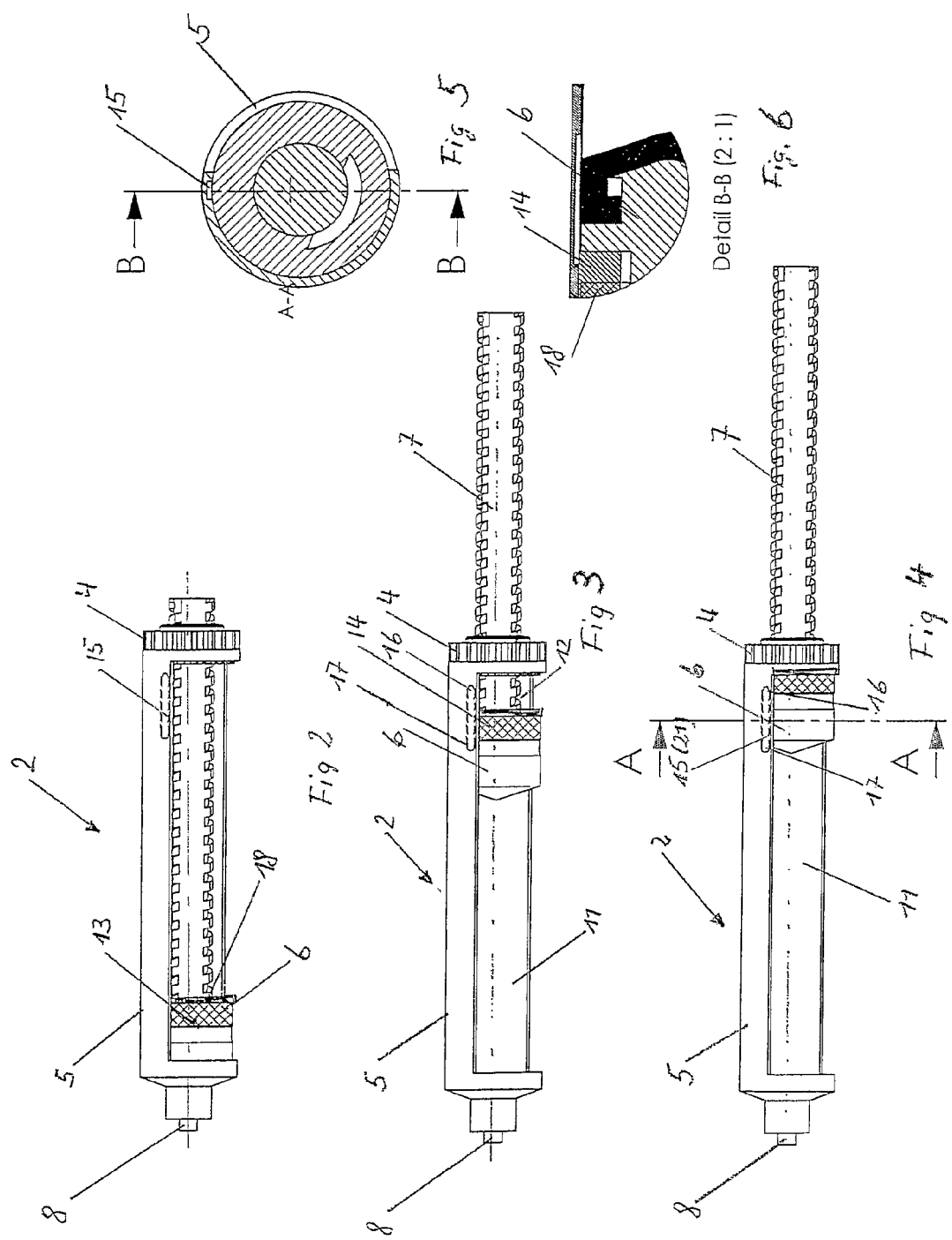

BIOPSY NEEDLE SYSTEM HAVING A PRESSURE GENERATING UNIT

CROSS-REFERENCE TO RELATED APPLICATIONS

This is a continuation of U.S. patent application Ser. No. 11/680,900, entitled "PRESSURE GENERATING UNIT", filed Mar. 1, 2007, which is a continuation of U.S. patent application Ser. No. 10/549,818, entitled "PRESSURE GENERATING UNIT", filed Sep. 20, 2005, now U.S. Pat. No. 7,762,961, which claims priority as a 371 application of PCT/EP2004/03328, filed Mar. 29, 2004, which claims priority to DE 10314240.1, filed Mar. 29, 2003.

MICROFICHE APPENDIX

None.

GOVERNMENT RIGHTS IN PATENT

None.

BACKGROUND OF THE INVENTION

1. Field of the Invention

The invention relates to a pressure generating unit, in particular a pressure generating unit that is arranged in the handpiece of a vacuum biopsy apparatus that is embodied as a type of syringe and whereby, by retracting the piston in the evacuated cylinder space when changing over to generating overpressure, the air supply is released by the position of the piston.

2. Description of the Related Art

A vacuum biopsy apparatus may include a pressure generating unit that is connected via a connecting line to a biopsy needle unit that is inserted into the tissue to be examined. The pressure generating unit and the needle unit are arranged parallel in the housing of a handpiece. A vacuum is generated in the needle space for removing the specimen by means of the pressure generating unit.

In order to be able to use the pressure generating unit for generating an overpressure as well, an aeration aperture is provided, and when it is released by the syringe piston, the vacuum that was generated is removed so that the air that has since penetrated can be compressed by means of the syringe piston.

Because not only the specimen is drawn into the specimen removal space by the vacuum, but also tissue fluid is drawn in, when the aeration aperture is briefly released, tissue fluid that has penetrated into the cylinder piston space can flow out into the interior of the handpiece, in particular when the pressure generating unit and/or the handpiece with the needle unit and the pressure generating unit connected thereto is in an unfavorable position. In order to prevent this, it has already been suggested to seal the aeration aperture by means of a sponge that is arranged on the exterior of the piston cylinder. However, this is not sufficient in all cases.

SUMMARY OF THE INVENTION

An object of the invention is, therefore, first to allow the air required for removing the vacuum to flow into the cylinder and, second, to reliably prevent an outflow of tissue fluid from contaminating the housing interior space of the handpiece.

This object may be obtained by connecting the evacuated cylinder space via a connecting line to the cylinder space that is under atmospheric pressure and is on the other piston side, and by providing an absorbent element on the piston spindle.

By arranging a connection between the two cylinder spaces that are divided by the piston, whereby the connection is released or closed by the position of the piston, and by arranging an absorbent element in the cylinder space that is under atmospheric pressure, on the one hand air can flow into the evacuated part of the cylinder from outside, and on the other hand the outflow of tissue fluid is drawn out of the evacuated cylinder part by the absorbent element. The length of the connection is selected so that the connecting line groove is over the absorbent element after the release of the connection for the inflow of air, with the aperture of the cylinder space ending under atmospheric pressure. This has the advantage that any tissue fluid that escapes during the brief opening of the connection is conducted directly into the element and absorbed by it.

The use of an air-permeable absorbent element furthermore has the advantage that the air coming in is filtered and thus particles cannot enter into the cylinder space.

It has proved particularly simple and cost-effective to use chemical pulp, in particular absorbent paper, as the material for the element.

It is advantageous that the element is held by means of a securing disk arranged on the piston spindle so that it cannot be displaced. This has the advantage that the element cannot migrate on the piston spindle during operation, which reduces the effectiveness of the element.

The invention, in one form thereof, is directed to a biopsy needle system. The biopsy needle system includes a cylinder with an open end and a cylinder wall. A piston is inserted in the open end such that a cylinder interior volume is defined between the piston and the cylinder, the piston being movable in the cylinder. A biopsy needle is connected to the cylinder. A ventilation groove is established in the cylinder wall only to a depth of a portion of a thickness of the cylinder wall. The ventilation groove is positioned such that the cylinder interior volume of the cylinder communicates with the ambient atmosphere when the piston is displaced to a position in the cylinder so as to establish an airflow through the ventilation groove past the piston.

The invention, another form thereof, is directed to a biopsy needle system. The biopsy needle system includes a cylinder with a cylinder wall, a cylinder floor and an open end. A piston is positioned in the cylinder for movement within the cylinder. The piston has a spindle. A spindle drive is mounted to the cylinder. The spindle drive is engaged with the spindle. A ventilation groove is formed in the interior of the cylinder wall only to a depth of a portion of a thickness of the cylinder wall. The ventilation groove extends toward the open end of the cylinder. The ventilation groove is configured to provide an airflow bypass of the piston as the piston passes over the ventilation groove. A biopsy needle is coupled to the cylinder, wherein one of a vacuum and an overpressure is communicated to the biopsy needle when the piston is moved by the spindle drive.

The invention, another form thereof, is directed to a biopsy needle system. The biopsy needle system includes a cylinder with an open end and a cylinder wall. A piston is inserted in the open end of the cylinder such that a cylinder interior volume is defined between the piston and the cylinder, the piston being movable in the cylinder. A biopsy needle is coupled to the cylinder. A ventilation groove is formed in the cylinder wall only to a depth of a portion of a thickness of the cylinder wall. The ventilation groove is positioned such that the cylinder interior volume communicates with the ambient atmosphere when the piston is displaced to a position so as to establish an airflow in the ventilation groove past the piston between the ambient atmosphere and the cylinder interior volume. An absorbent element is carried by the piston. The absorbent element is configured to engage the ventilation groove to receive the airflow.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 2 shows the pressure generating unit with piston pushed in (partial cut-away);

FIG. 3 shows the pressure generating unit after generating a vacuum by retracting the piston;

FIG. 4 shows the pressure generating unit after releasing the connection for aeration;

FIG. 5 shows a section A-A through FIG. 4; and

FIG. 6 shows a section B-B through FIG. 5

Corresponding reference characters indicate corresponding parts throughout the several views. The exemplifications set out herein illustrate one embodiment of the invention, in one form, and such exemplifications not to be construed as limiting the scope of the invention in any manner.

DETAILED DESCRIPTION OF THE INVENTION

Figure 1:
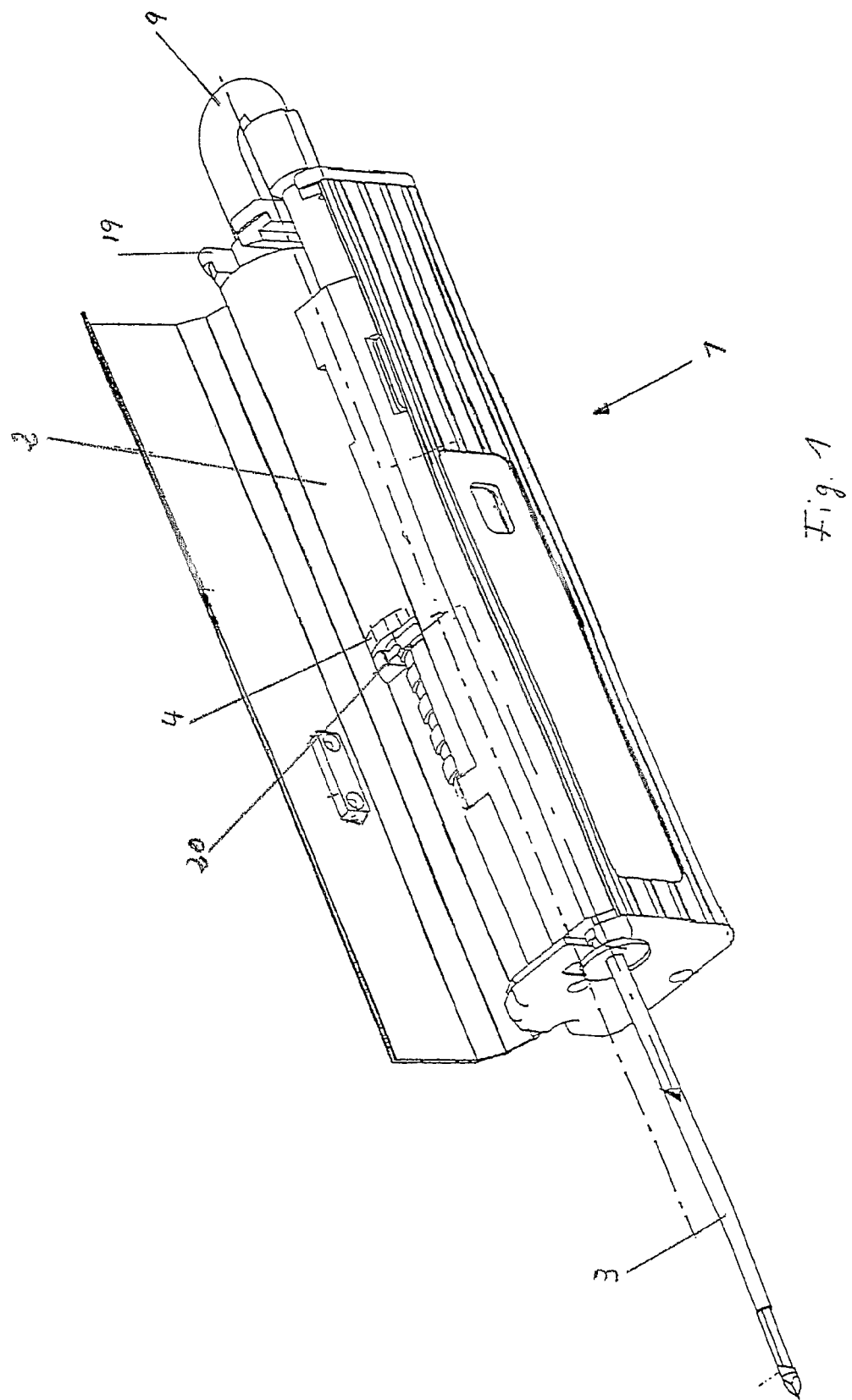
FIG. 1 shows a biopsy apparatus having a pressure generating unit configured in accordance with an embodiment of the present invention.

FIG. 1 illustrates a biopsy apparatus 1 in which the pressure generating unit 2 is housed in a housing with a needle unit 3 that is situated parallel thereto. The pressure generating unit is driven, for example, via an electro-gear motor (not shown) via the toothed wheel 4.

The pressure generating unit 2, which is constructed as a type of syringe, comprises a cylinder 5 in which a piston 6 is longitudinally displaceable by means of a piston spindle 7. The piston spindle drive comprises a toothed wheel 4 mounted on the open end of the cylinder, whereby the center of the toothed wheel is embodied as a spindle nut that interacts with the piston spindle 7 mounted therein. The piston spindle 7 is moved to the connector 8 or to the toothed wheel 4 by means of the toothed wheel 4, depending on the direction of rotation of the motor, via a pinion (not shown) that sits on the shaft of an electromotor. The cylinder of the pressure generating unit has at one end a connector 8 for a connecting piece 9 that is connected to the biopsy needle unit 3. Arranged on the side opposite the connector is a toothed wheel 4 with an interior spindle thread (spindle nut) that interacts with the piston spindle 7 so that with each rotation of the toothed wheel the piston 6 travels a precisely defined path to the one or the other side, depending on motor rotation. The toothed wheel can be mounted in the open cylinder end.

Depending on the direction of rotation, the piston 3 can be moved via the toothed wheel/spindle drive to the cylinder floor or away from the cylinder floor to the toothed wheel. The pressure generating unit is fitted for instance in a biopsy apparatus as it is illustrated in FIG. 1. The biopsy apparatus may include a hand piece, into which a hollow biopsy needle is placed, wherein part of the part of the biopsy needle that protrudes out beyond the hand piece with its sample-removing space can be fired into the tissue to be examined. The tissue is sucked into the sample-removing space by a vacuum, subsequently severed by a sample-severing device, and subsequently removed. To eject the sample, the vacuum-generating device is used for generating a positive pressure. The vacuum/pressure-generating device and further control and supply devices are integrated in the housing of the hand piece. The connecting element of the biopsy needle to the vacuum/pressure-generating unit is arranged directly on the housing. The distance between the housing wall 19 and insertion groove 20 for the piston spindle is selected so that the pressure generating unit cannot move in the longitudinal axis and the toothed wheel 4 is thus supported in the cylinder. When the piston is retracted to just in front of the aperture for the connecting line 21, here a groove 15 in the cylinder wall, i.e., in the direction of the toothed wheel 4, a vacuum forms in the biopsy needle system (see FIG. 3). After the air supply is released in the cylinder space 11 (opening of connecting line, groove is opened)—as described in the following—the underpressure previously created in the biopsy needle system (see FIG. 4) is removed by the inflow of air. If the piston is moved in the direction of the connector 8 after the air has flowed in, overpressure is created in the system.

The piston spindle carries the piston 10 with a rubber jacket on the side opposite the drive, i.e., on the connector side. On the interior piston cylinder wall, the rubber jacket of the piston seals the left-hand cylinder space 11 (space in front of the connector) from the cylinder space 12. In other words, if the connector support 8 is connected to the biopsy needle unit via the connecting piece 9 and the biopsy needle is inserted into tissue, for example, an underpressure occurs in the biopsy needle system due to the displacement of the piston to the drive side. The cylinder space 12 is furthermore under atmospheric pressure. Arranged on the side wall 13 of the piston, which is in the cylinder space 12, is an absorbent element 14 that is penetrated coaxially by the piston spindle and that is held, for example by means of a securing disk 18 that is attached to the piston spindle. The element is round and is situated so that it acts as a minor seal against the interior cylinder wall of the cylinder. In order to make it easy to pass over the piston spindle, the element embodied as a punched disk is slit. The element can comprise a plurality of individual disks that are approx. 1 mm thick. It can also be a single part, however. It extends approx. 3 mm. The element is placed directly on the piston side wall 13 and is held by the securing disk. A groove 15 is worked into the interior wall of the cylinder wall as a connection 21 on the cylinder part adjacent to the toothed wheel 4. As FIG. 5 illustrates, the depth of the groove is approximately half the wall thickness. The groove length (FIG. 5) is selected so that the groove ends when the air supply is released to the center of the absorbent element 14 and the cylinder space 11 to be aerated is connected to the exterior atmospheric pressure via the groove. In this position the groove has to a certain extent two "apertures." The one "aperture 17" ends in the cylinder space 11; the other "aperture 16" ends above the element 14 when the piston is brought to the open position (see FIG. 4).

An embodiment of a biopsy apparatus may include, for example, a hand piece with drive elements, into which a biopsy needle is placed, wherein part of the part of the biopsy needle that protrudes out beyond the hand piece with its sample-removing space can be fired into the tissue to be examined and the tissue sample to be investigated forces its way into the opening of the sample-removing space by negative pressure and is subsequently severed by a longitudinally movable sample-severing device, and subsequently removed from the sample-removing space. The two longitudinal side edges of the sample-removing space are formed as cutting edges and, during and/or after opening of the sample-removing space, the cutting edges are moved slightly forwards and back repeatedly by moving of the biopsy needle, wherein the lateral cutting effect is supported in particular by the applied negative pressure in the biopsy needle. When employing the vacuum biopsy equipment in such a biopsy device, or as previously described, it has been demonstrated that the suction action of the pressure generating unit 2 is so strong that, depending on the position of the biopsy apparatus when the specimen is drawn, more or less tissue fluid can enter into the pressure generating unit 2. By arranging a groove 15 in the interior of the cylinder, which groove is primarily needed because of the removal of the underpressure, it is not always possible to avoid the outflow of tissue fluid during the brief opening of the aeration aperture and its subsequent closing.

However, because the groove is designed so that the "aperture 16" ends over the absorbent element, the tissue fluid is absorbed and no tissue fluid flows into the housing of the biopsy handpiece. When the "aperture 16" of the groove is released (see FIG. 4) the air can travel from the cylinder space 9 to the absorbent element via the groove into the cylinder space 11 and remove the vacuum there. In other words, the air is filtered prior to its entering the cylinder space 11. Due to the electronic components installed there, it is absolutely necessary to prevent the flow of tissue fluid into the housing of the handpiece of the biopsy apparatus because wet cleaning of the handpiece can lead to serious damage to the electronics.

In the exemplary embodiment, an interior groove is provided as a connection from the cylinder space 11 to the cylinder space 12. The connection can also be embodied as an exterior line or as a line that is integrated into the cylinder jacket. What is important for solving the problem is that the tissue fluid that can escape when the vacuum is removed can be intentionally conducted so that the tissue fluid is absorbed by means of an absorbent element and does not enter into the housing.

LIST OF PARTS

1) Biopsy apparatus
2) Pressure generating unit
3) Needle unit
4) Toothed wheel
5) Cylinder
6) Piston
7) Piston spindle
8) Connector
9) Connection piece
10)
11) Cylinder space
12) Cylinder space
13) Side wall
14) Absorbent element
15) Groove
16) Aperture
17) Aperture
18) Securing disk
19) Housing wall
20) Insertion groove
21) Connection line While this invention has been described with respect to an embodiment of the invention, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy needle system, comprising:
   a cylinder with an open end and a cylinder wall;
   a piston inserted in the open end such that a cylinder interior volume is defined between the piston and the cylinder, the piston being movable in the cylinder;
   a biopsy needle connected to the cylinder; and
   a ventilation groove established in the cylinder wall only to a depth of a portion of a thickness of the cylinder wall, the ventilation groove being positioned such that the cylinder interior volume of the cylinder communicates with the ambient atmosphere when the piston is displaced to a position in the cylinder so as to establish an airflow through the ventilation groove past the piston.

2. The biopsy needle system of claim 1, further comprising an absorbent element carried by the piston, the absorbent element being positioned such that the absorbent element filters air that moves from the ambient atmosphere through the ventilation groove to the cylinder interior volume.

3. The biopsy needle system of claim 1, further comprising an absorbent element carried by the piston, the absorbent element being configured to engage the ventilation groove.

4. The biopsy needle system of claim 1, wherein the airflow is a dissipation of a vacuum in the cylinder interior volume of the cylinder.

5. The biopsy needle system of claim 1, wherein the ventilation groove is located adjacent the open end of the cylinder.

6. The biopsy needle system of claim 1, wherein the depth of the ventilation groove in the cylinder wall is approximately half of the thickness of the cylinder wall.

7. A biopsy needle system, comprising:
   a cylinder with a cylinder wall, a cylinder floor and an open end;
   a piston positioned in the cylinder for movement within the cylinder, the piston having a spindle;
   a spindle drive mounted to the cylinder, the spindle drive being engaged with the spindle;
   a ventilation groove formed in the interior of the cylinder wall only to a depth of a portion of a thickness of the cylinder wall, the ventilation groove extending toward the open end of the cylinder, the ventilation groove being configured to provide an airflow bypass of the piston as the piston passes over the ventilation groove; and
   a biopsy needle coupled to the cylinder, wherein one of a vacuum and an overpressure is communicated to the biopsy needle when the piston is moved by the spindle drive.

8. The biopsy needle system of claim 7, wherein a cylinder interior volume is defined between the piston and the cylinder floor, and wherein the cylinder interior volume of the cylinder communicates with the ambient atmosphere when the piston is displaced to a position in the cylinder so as to establish the airflow bypass of the piston via the ventilation groove.

9. The biopsy needle system of claim 7, wherein a cylinder interior volume is defined between the piston and the cylinder floor, and further comprising an absorbent element carried by the piston, the absorbent element being positioned such that the absorbent element filters air that moves through the ventilation groove to the cylinder interior volume.

10. The biopsy needle system of claim 7, further comprising an absorbent element carried by the piston, the absorbent element being configured to engage the ventilation groove.

11. The biopsy needle system of claim 7, wherein the ventilation groove is in an upper part of the cylinder, the upper part being at an opposite end portion of the cylinder from that of the cylinder floor.

12. The biopsy needle system of claim 7, wherein the ventilation groove is selectively openable to dissipate a vacuum in the cylinder by a movement of the piston over a predefined displacement interval such that an inflow of air is established through the ventilation groove past the piston.

13. The biopsy needle system of claim 7, wherein the ventilation groove is located adjacent the open end of the cylinder.

14. The biopsy needle system of claim 7, wherein the depth of the ventilation groove in the cylinder wall is approximately half of the thickness of the cylinder wall.

15. The biopsy needle system of claim 7, wherein the spindle drive includes a spindle nut mounted on the open end of the cylinder.

16. The biopsy needle system of claim 7, wherein the spindle drive is a wheel mounted on the open end of the cylinder, the wheel having teeth therearound.

17. A biopsy needle system, comprising:

a cylinder with an open end and a cylinder wall;

a piston inserted in the open end of the cylinder such that a cylinder interior volume is defined between the piston and the cylinder, the piston being movable in the cylinder;

a biopsy needle coupled to the cylinder;

a ventilation groove formed in the cylinder wall only to a depth of a portion of a thickness of the cylinder wall, the ventilation groove being positioned such that the cylinder interior volume communicates with the ambient atmosphere when the piston is displaced to a position so as to establish an airflow in the ventilation groove past the piston between the ambient atmosphere and the cylinder interior volume; and an absorbent element carried by the piston, the absorbent element being configured to engage the ventilation groove to receive the airflow.

18. The biopsy needle system of claim 17, wherein the absorbent element is positioned such that the absorbent element filters air that moves through the ventilation groove to the cylinder interior volume, and absorbs fluid that moves through the ventilation groove from the cylinder interior volume toward the ambient atmosphere.

19. The biopsy needle system of claim 17, wherein the depth of the ventilation groove in the cylinder wall is approximately half of the thickness of the cylinder wall.

* * * * *